United States Patent

Joseph et al.

[11] Patent Number: 6,107,219
[45] Date of Patent: Aug. 22, 2000

[54] BREATHABLE BACKING FOR AN ADHESIVE ARTICLE

[75] Inventors: Eugene G. Joseph, Arden Hill; Steven C. Stickels, Woodbury, both of Minn.

[73] Assignee: 3M Innovative Properties Company, St. Paul, Minn.

[21] Appl. No.: 09/022,303

[22] Filed: Feb. 11, 1998

[51] Int. Cl.[7] ............................... D04H 3/12; B32B 7/12
[52] U.S. Cl. .................. 442/361; 442/347; 442/362; 442/363; 442/364; 442/400; 442/151; 428/343
[58] Field of Search ..................... 442/340, 341, 442/347, 361, 362, 363, 364, 400, 401, 151; 428/343

[56] References Cited

U.S. PATENT DOCUMENTS

| | | | |
|---|---|---|---|
| 4,595,001 | 6/1986 | Potter et al. | 128/156 |
| 5,124,194 | 6/1992 | Kawano | 442/363 X |
| 5,230,701 | 7/1993 | Meyer et al. | 602/76 |
| 5,238,733 | 8/1993 | Joseph et al. | 428/284 |
| 5,382,400 | 1/1995 | Pike et al. | 264/168 |
| 5,496,603 | 3/1996 | Riedel et al. | 442/151 X |
| 5,601,851 | 2/1997 | Terakawa | 425/72.2 |
| 5,613,942 | 3/1997 | Lucast et al. | 602/52 |
| 5,614,310 | 3/1997 | Delgado et al. | 428/316.6 |
| 5,798,305 | 8/1998 | Horiuchi | 442/361 |

FOREIGN PATENT DOCUMENTS

| | | | |
|---|---|---|---|
| 091800 | 10/1983 | European Pat. Off. . | |
| 0 277 710 A2 | 1/1988 | European Pat. Off. | D04H 1/56 |
| 353972 | 2/1990 | European Pat. Off. . | |
| 0 368 541 A1 | 5/1990 | European Pat. Off. | A61F 13/02 |
| 0 420 256 A2 | 4/1991 | European Pat. Off. | B29C 67/14 |
| 0 432 763 A1 | 6/1991 | European Pat. Off. | D04H 1/56 |
| WO 92/16361 | 10/1992 | WIPO | B32B 3/02 |

*Primary Examiner*—Daniel Zirker
*Attorney, Agent, or Firm*—Gary L. Griswold; Robert W. Sprague; William J. Bond

[57] ABSTRACT

There is provided pressure-sensitive adhesive coated breathable nonwoven tape backing substrate where the nonwoven tape backing comprises a fibrous nonwoven web formed in part by multicomponent fibers having an adhesive component region. The multicomponent fibers are distributed throughout the width dimension of the nonwoven tape backing such that adhesive component region is exposed on both outer faces of the nonwoven tape backing. The adhesive component region is preferably a pressure-sensitive adhesive region formed by hot melt coextrusion of at least two components to form the multicomponent fibers. A pressure-sensitive adhesive tape layer is coated onto at least one face of the nonwoven tape backing which pressure-sensitive adhesive tape layer is preferably of the same type of adhesive as that forming the adhesive region of the multicomponent fiber or is at least compatible with the adhesive region of the multicomponent fiber such that the adhesive has enhanced adhesive properties to the pressure-sensitive adhesive tape layer.

25 Claims, 1 Drawing Sheet

BREATHABLE BACKING FOR AN ADHESIVE ARTICLE

BACKGROUND OF THE INVENTION

The invention relates to pressure-sensitive adhesive products having a breathable backing particularly for adhering to skin or like surfaces.

Pressure-sensitive adhesive tapes and the like are used in a wide variety of applications where there is a need for a breathable backing. These tapes generally are designed to adhere to a surface that is a source of moisture such as skin; however, porous articles can be a moisture source if they are in communication with a fluid source. Tapes designed to adhere to skin include, for example, medical tapes such as wound or surgical dressings, athletic tapes, surgical drapes, or tapes or tabs used in adhering medical devices such as sensors, electrodes, ostomy appliances or the like. Lack of breathability with these tape products can result in overhydration and sometimes maceration of the skin. For example, U.S. Pat. No. 5,614,310 suggests using a backing having moisture vapor transmission rate (MVTR) value of at least 500 g/m$^2$/day (measured using ASTM E 96–80 at 40° C.).

A discontinuous adhesive coating on a breathable backing allows the skin to breathe, at least in the areas of the backing not coated with adhesive. This approach is disclosed in U.S. Pat Nos. 4,595,001 Cotter); U.S. Pat. No. 5,613,942; EP 353972; and EP 91800. These patent documents generally teach intermittent coating of adhesives onto different backings. For example, U.S. Pat No. 5,613,942 describes printing pressure-sensitive adhesives using a release coated calender roll process similar to Gravure printing. This patent also teaches screen-printing. However, pattern coating or printing of adhesives in this manner is problematic as it generally requires solvents, which are environmentally problematic, It would be preferred from environmental, manufacturing (e.g. elimination of the need for expensive solvent recovery) and performance perspectives to have adhesives coatable directly from a melt phase.

With polyolefin type tape backings and like low energy materials there is often a need to increase the surface energy of the backing material to allow the pressure-sensitive adhesive to remain securely bonded to the backing. This is generally termed priming and can be done with surface treatments such as flame treatments, corona treatment or like oxidizing surface treatments. These are generally acceptable but require a separate process step complicating manufacture of the tape product. It is also known to apply primer coatings to a surface of the backing. These often are curable coatings as are disclosed in U.S. Pat. Nos. 5,639,546; 5,631,079; and 5,503,927. Although effective, they require one or more further process steps and can occlude the pores of a porous backing. Melt additives and tie layers are also often used with film backings, which eliminate the need for a separate priming step however these films are generally not porous. The invention is directed at providing a pressure-sensitive adhesive tape backing product that is simple to manufacture, does require a separate priming step, and also is extremely breathable.

SUMMARY OF THE INVENTION

The invention relates to a pressure-sensitive adhesive coated breathable nonwoven tape backing substrate where the nonwoven tape backing comprises a fibrous nonwoven web formed in part by multicomponent fibers having an adhesive component region. The multicomponent fibers are distributed throughout the width dimension of the nonwoven tape backing such that adhesive component region is exposed on both outer faces of the nonwoven tape backing. The adhesive component region is preferably a pressure-sensitive adhesive region formed by hot melt coextrusion of the adhesive component and at least one nonadhesive component to form the multicomponent fibers. The nonwoven tape backing is preferably formed simultaneously with the formation of the multicomponent fibers or simultaneously with the collection of the multicomponent fibers into the nonwoven backing.

The pressure-sensitive adhesive tape layer is coated onto at least one face of the nonwoven tape backing which pressure-sensitive adhesive tape layer is preferably of the same type of adhesive as that forming the adhesive region of the multicomponent fiber or is at least compatible with the adhesive region of the multicomponent fiber such that the adhesive has enhanced adhesive properties to the pressure-sensitive adhesive tape layer. By enhanced adhesive properties it is meant that the pressure-sensitive adhesive tape layer adheres more strongly to the adhesive region material than the non-adhesive region material of the multicomponent fiber. Preferably the pressure-sensitive adhesive tape layer is breathable to provide a breathable tape product.

DETAILED DESCRIPTION OF THE PREFERRED EMBODIMENTS

The invention pressure-sensitive adhesive coated nonwoven tape backing is formed from coherent multicomponent fibers having at least one pressure-sensitive adhesive region or layer and at least one non-pressure-sensitive adhesive region or layer. The fibers forming the nonwoven tape backing are intimately entangled each with the other in the form of a coherent breathable fibrous nonwoven tape backing. Suitable nonwoven tape backings can be formed as melt blown microfiber webs using the apparatus discussed, for example, in Wente, Van A., "Superfine Thermoplastic Fibers", *Industrial Engineering Chemistry*, Vol. 48, pages 1342–1346, Wente, Van A. et al., "Manufacture of Superfine Organic Fibers", Report No. 4364 of the Navel Research Laboratories, published May 25, 1954, and in U.S. Pat Nos. 3,849,241; 3,825,379; and others. These microfine fibers are termed melt blown fibers or blown microfibers (BMF) and are generally substantially continuous and form into a coherent web between the exit die orifice and a collecting surface by entanglement of the microfibers due in part to the turbulent airstream in which the fibers are entrained. Other conventional melt spinning type processes, such as spunbond processes where the fibers are collected in a web form immediately upon fiber formation, can also be used to form the invention nonwoven tape backing. Generally, the fibers are 100 microns or less in diameter when formed by melt spinning type processes, preferably 50 microns or less. The multicomponent fibers, if formed by the melt blown process, can be produced as described in U.S. Pat. Nos. 5,176,952 (Joseph et al); 5,232,770 (Joseph); 5,238,733 (Joseph et al); 5,258,220 (Joseph); or 5,248,455 (Joseph et al). The multicomponent fiber can also be produced by a spunbond process as are disclosed in U.S. Pat. Nos. 5,695,868 (McCormach); 5,336,552 (Strack et al); 5,545,464 (Stokes);

5,382,400; 5,512,358 (Shawyer et al); or 5,498,463 (McDowall et al).

Melt blown processes are particularly preferred because they form autogenously bonded webs that typically require no further processing to effectively bond the fibers together into a coherent web. The melt blown processes used in the formation of multilayer microfibers as disclosed in the Joseph (et al.) patents listed above are particularly suitable for use in making the multilayer microfibers of the present invention. Such processes use hot (e.g., equal to or about 20° C. to about 30° C. higher than the polymer melt temperature), high-velocity air to draw out and attenuate extruded polymeric material from a die, which will generally solidify after traveling a relatively short distance from the die. The resultant fibers are termed melt blown fibers and are generally substantially continuous. The fibers form into a coherent web between the exit die orifice and a collecting surface by entanglement of the fibers due in part to the turbulent airstream in which the fibers are entrained.

For example, U.S. Pat. No. 5,238,733 (Joseph et al.) describes forming a multicomponent melt blown microfiber web by feeding two separate flow streams of organic polymeric material into a separate splitter or combining manifold. The split or separated flow streams are generally combined immediately prior to the die or die orifice. The separate flow streams are preferably established into melt streams along closely parallel flow paths and combined where they are substantially parallel to each other and to the flow path of the resultant combined multilayered flow stream. This multilayered flow stream is then fed into the die and/or die orifices and through the die orifices. Air slots are disposed on either side of a row of the die orifices directing uniform heated air at high velocities at the extruded multicomponent melt streams. The hot high-velocity air draws and attenuates the extruded polymeric material which solidifies after traveling a relatively short distance from the die. Single layer microfibers can be made in an analogous manner with air attenuation using a single extruder, no splitter, and a single port feed die.

The solidified or partially solidified fibers form an interlocking network of entangled fibers, which are collected as a coherent web. The collecting surface can be a solid or perforated surface in the form of a flat surface or a drum, a moving belt, or the like. If a perforated surface is used, the backside of the collecting surface can be exposed to a vacuum or low-pressure region to assist in the deposition of the fibers. The collector distance is generally about 7 centimeters (cm) to about 130 cm from the die face. Moving the collector closer to the die face, e.g., about 7 cm to about 30 cm, will result in stronger inter-fiber bonding and a less lofty web.

The temperature of the separate polymer flowstreams is typically controlled to bring the polymers to substantially similar viscosities. When the separate polymer flowstreams converge, they should generally have an apparent viscosity in the melt (i.e., at melt blowing conditions) of about 150 poise to about 800 poise, as determined using a capillary rheometer. The relative viscosities of the separate polymeric flowstreams to be converged should generally be fairly well matched.

The size of the polymeric fibers formed depends to a large extent on the velocity and temperature of the attenuating airstream, the orifice diameter, the temperature of the melt stream, and the overall flow rate per orifice. Typically, fibers having a diameter of no greater than about 10 microns can be formed, although coarse fibers, e.g., up to about 50 microns or more, can be prepared using a melt-blown process, and up to about 100 microns, can be prepared using a spun bond process. The webs formed can be of any suitable thickness for the desired and intended end use. Generally, a thickness of about 0.01 cm to about 5 cm is suitable for most applications.

The multicomponent fibers can be mixed with other fibers in the backing, such as other melt spun fibers, staple fibers, including inorganic and organic fibers, such as thermoplastic fibers, carbon fibers, glass fibers, mineral fibers, or organic binder fibers, as well as fibers of different polymers. The pressure-sensitive adhesive fibers of the present invention can also be mixed with particulates, such as sorbent particulate material, fumed silica, carbon black, glass beads, glass bubbles, clay particles, metal particles, and the like. Typically, this is done prior to the fibers being collected by entraining particulates or other fibers in an airstream, which is then directed to intersect with the fiber streams. Alternatively, other polymer materials can be simultaneously melt processed with the multicomponent fibers of the present invention to form webs containing more than one type of melt processed fiber, preferably, melt blown microfiber. Webs having more than one type of fiber are referred to herein as having commingled constructions. In commingled constructions, the various types of fibers can be intimately mixed forming a substantially uniform cross-section, or they can be in separate layers. The web properties can be varied by the number of different fibers used, the number of layers or regions employed, and the layer or region arrangement. Other materials, such as surfactants or binders can also be incorporated into the web before, during, or after its collection, such as by the use of a spray jet.

The adhesive component layer or region and non-adhesive component layer or region are present in separate distinct regions in a conjugate multicomponent fiber. For example, multicomponent fiber layers or regions can be in the form of two, or more, overlaying layered fibers, sheath-core or concentric layered fiber arrangements or in "island in the sea" type fiber layer structures. One component region would comprise the adhesive component layer or region and a second component region would comprise the non-adhesive material layer or region. Generally the adhesive fiber component region will provide at least a portion of the exposed outer surface of the multicomponent conjugate fiber. Preferably, the individual components of the multicomponent conjugate fibers will be present substantially continuously along the fiber length in discrete zones, which zones preferably extend along the entire length of the fibers. The individual fibers generally are of a fiber diameter of less than 100 microns, preferably less than 50 microns or 25 microns for microfibers.

Alternatively, conjugate multicomponent fibers can be formed by a spunbond process such as described in U.S. Pat. No. 5,382,400 where separate polymer flow streams are fed via separate conduits to a spinneret for producing conjugate multicomponent fibers. Generally, these spinnerets include a housing containing a spin pack with a stack of plates which form a pattern of openings arranged to create flow paths for directing the separate polymer components separately through the spinneret. The spinneret can be arranged to extrude the polymer vertically or horizontally in one or more rows of fibers.

An alternative arrangement for forming melt blown conjugate multicomponent fibers is described for example, in U.S. Pat. No. 5,601,851. The polymer flow streams are separately fed to each individual die orifice by the use of grooves cut in a distributing and/or separating plate. This arrangement can be used to separately extrude different polymers from different individual orifices to provide separate distinct fibers which form a coherent entangled web having a substantially uniform distribution of the differing fibers. By feeding two, separate polymers to an individual die orifice a conjugate multicomponent fiber can be formed. The apparatus described is suitably used in a melt blowing type arrangement where the die orifices are formed in a row along the die.

Figure 1:
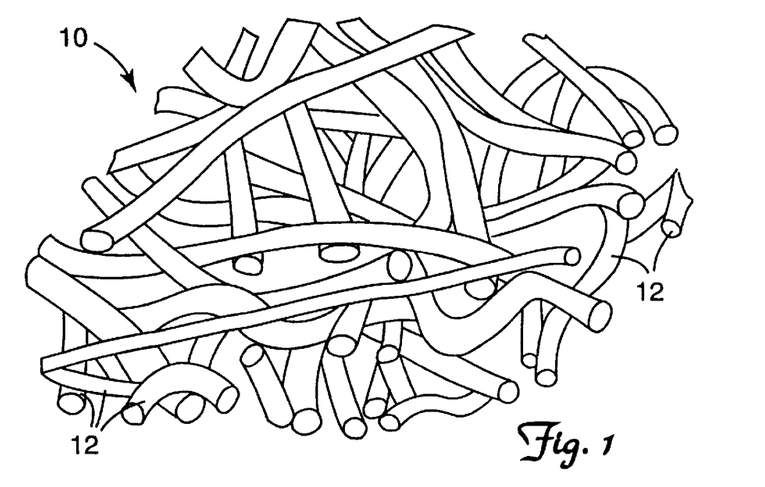
FIG. 1 is a perspective view of a nonwoven tape backing of the present invention made from multicomponent fibers.
Figure 2:
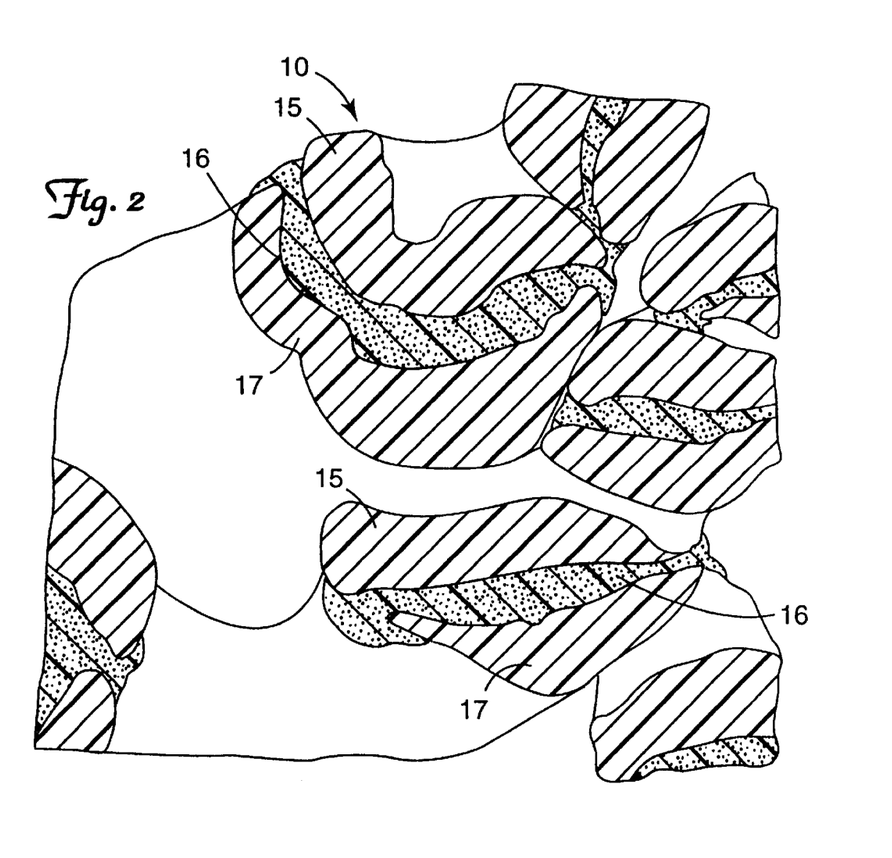
FIG. 2 is a cross-sectional view of the nonwoven tape backing of FIG. 1 at a higher magnification showing a three layer construction of the fibers.

FIG. 1 is an illustration of a nonwoven web 10 prepared from multilayered fibers 12 according to the present invention. FIG. 2 is a cross-sectional view of the nonwoven web 10 of FIG. 1 at higher magnification showing a three layer construction of the fibers 12. The multilayered fibers 12 each have three discrete overlaying layers of polymeric material. There is one layer of an adhesive material, and two layers 15,17 of a non-adhesive material. It is significant to note, that the surface of the fibers have exposed edges of the layers of both materials. Thus, the fibers, and hence, the nonwoven webs, of the present invention, can demonstrate properties associated with both types of materials simultaneously. Although FIG. 1 illustrates a fiber having three layers of material, the fibers of the present invention can include two or many more layers, e.g., hundreds of layers. Thus, the coherent fibers of the present invention can include, for example, only one type of adhesive material in one layer, two or more different types of adhesive compositions in two or more layers, layered with one or more non-adhesive material(s) in one or more layers. Each of the layer materials can be a mixture of different adhesive materials and/or non-adhesive materials.

The adhesive component region material preferably comprises an extrudable pressure-sensitive adhesive suitable for melt blowing (generally this requires the adhesive to have an apparent viscosity of from 150 to 800 poise, under melt-processing conditions measured by a capillary rheometer) or other fiber spinning processes such as spunbond processing. With conjugate fibers of different polymers or blends formed from a single die or spinneret, the viscosities of the separate polymer flowstreams should be fairly closely matched for uniform fiber and web formation, but this is not required. Generally matching viscosities will ensure more uniformity in the conjugate fibers formed in terms of minimizing polymer mixing, which mixing can result in fiber breakage and formation of shot (small particulate polymer material), and lower web tensile properties. However, the presence of discontinuous fibers or shot is not necessarily undesirable as long as the nonwoven tape backing has the desired overall strength.

The particular adhesive used in forming discrete multicomponent, conjugate fibers depends on the adhesive selected for the pressure-sensitive adhesive tape layer and the non-adhesive component region material selected. The pressure-sensitive adhesive selected is generally any hot melt extrudable copolymer or composition having a viscosity in the melt phase suitable for fiber forming by melt processing.

Suitable classes of pressure-sensitive adhesives include polyacrylate adhesives, polyalphaolefin adhesives, polyvinyl acrylates, rubber resin adhesives polydiorganosiloxane polyurea compolymers, mixtures or the like. Suitable rubber resin adhesives would include those formed using a tackified elastomer where a preferred elastomer is an A–B type block copolymer wherein the A blocks and B blocks are configured in linear (e.g. diblock or triblock copolymer), radial or star configurations. The A block is formed of a monoalkenylarene, preferably a polystyrene block having a molecular weight between 4000 and 50,000, preferably between 7000 and 30,000. The A block content is preferably about 10 to 50 weight percent, preferably about 10 to 30 weight percent of the block copolymer. Other suitable A blocks may be formed from alpha-methylstyrene, t-butylstyrene and other ring alkylated styrenes, as well as mixtures thereof. The B block is formed of an elastomeric conjugated diene, generally polyisoprene, polybutadiene or copolymers thereof having an average molecular weight from about 5000 to about 500,000, preferably from about 50,000 to about 200,000. The B block dienes can also be hydrogenated. The B block content is generally 90 to 50 percent, preferably 90 to 70 percent by weight. The tackifying components for the elastomer based adhesives generally comprise a solid tackifying resin and/or a liquid tackifier or plasticizer. Preferably, the tackifying resins are selected from the group of resins at least partially compatible with the polydienes B block portion of the elastomer. Although not preferred, generally a relatively minor amount of the tackifying resin can include resins compatible with the A block, which when present are generally termed end block reinforcing resins. Generally, end block resins are formed from aromatic monomer species. Suitable liquid tackifiers or plasticizers for use in the adhesive composition include napthenic oils, paraffin oils, aromatic oils, mineral oils or low molecular weight rosin esters, polyterpenes and C-5 resins. Some suitable B-block compatible solid tackifying resins include C-5 resins, resin esters, polyterpenes and the like.

The tackifier portion of the pressure-sensitive adhesive generally comprises from 20 to 300 parts per 100 parts of the elastomer phase. Preferably, this is predominately solid tackifier, however, from 0 to 25 weight percent, preferably 0 to 10 weight percent of the adhesive composition can be liquid tackifier and/or plasticizer.

Suitable rubber resin adhesives for melt blown processing are discussed in EP 658351 which exemplifies melt blown fibrous synthetic rubber resin type adhesives used in a disposable absorbent article to either immobilize particulate sorbents or used as a pressure-sensitive adhesive attachment (e.g., for a sanitary napkin). Suitable adhesives exemplified are styrene-isoprene-styrene triblock block copolymer based, where the copolymer has coupling efficiencies ranging from 42 to 65 percent (e.g., 58 to 35 percent polystyrene-polyisoprene diblock material would be present), tackified with C-5 hydrocarbon resins (WINGTACK PLUS and WINGTACK 10 available from Goodyear) and stabilized with antioxidants.

Generally, depending on the fiber formation process, suitable antioxidants and heat stabilizers could be used in the present invention to prevent the degradation of the adhesive during the fiber forming process or in use. Also, other conventional additives could be used such as UV absorbents, pigments, particulates, staple fibers or the like.

Suitable poly(acrylates) are derived from: (A) at least one monofunctional alkyl (meth)acrylate monomer (i.e., alkyl acrylate and alkyl methacrylate monomer); and (B) at least one monofunctional free-radically copolymerizable reinforcing monomer. The reinforcing monomer has a homopolymer glass transition temperature ($T_g$) higher than that of the alkyl (meth)acrylate monomer and is one that increases the glass transition temperature and modulus of the resultant copolymer. Monomers A and B are chosen such that a copolymer formed from them is extrudable and capable of forming fibers. Herein, "copolymer" refers to polymers containing two or more different monomers, including terpolymers, tetrapolymers, etc.

Preferably, the monomers used in preparing the pressure-sensitive adhesive copolymer fibers of the present invention include: (A) a monofunctional alkyl (meth)acrylate monomer that, when homopolymerized, generally has a glass transition temperature of no greater than about 0° C.; and (B) a monofunctional free-radically copolymerizable reinforcing monomer that, when homopolymerized, generally has a glass transition temperature of at least about 10° C. The glass transition temperatures of the homopolymers of monomers A and B are typically accurate to within ±5° C. and are measured by differential scanning calorimetry.

Monomer A, which is a monofunctional alkyl acrylate or methacrylate (i.e., (meth)acrylic acid ester), contributes to the flexibility and tack of the copolymer. Preferably, monomer A has a homopolymer $T_g$ of no greater than about 0° C. Preferably, the alkyl group of the (meth)acrylate has an average of about 4 to about 20 carbon atoms, and more preferably, an average of about 4 to about 14 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples include, but are not limited to, poly-ethoxylated or -propoxylated methoxy (meth)acrylate (i.e., poly(ethylene/propylene oxide) mono-(meth)acrylate) macromers (i.e., macromolecular monomers), polymethylvinyl ether mono (meth)acrylate macromers, and ethoxylated or propoxylated nonyl-phenol acrylate macromers. The molecular weight of such macromers is typically about 100 grams/mole to about 600 grams/mole, and preferably, about 300 grams/mole to about 600 grams/mole. Combinations of various monofunctional monomers categorized as an A monomer can be used to make the copolymer used in making the fibers of the present invention.

Monomer B, which is a monofunctional free-radically copolymerizable reinforcing monomer, increases the glass transition temperature of the copolymer. As used herein, "reinforcing" monomers are those that increase the modulus of the adhesive, and thereby its strength. Preferably, monomer B has a homopolymer $T_g$ of at least about 10° C. More preferably, monomer B is a reinforcing monofunctional (meth)acrylic monomer, including an acrylic acid, a methacrylic acid, an acrylamide, and an acrylate. Examples of monomer B include, but are not limited to, acrylamides, such as acrylamide, methacrylamide, N-methyl acrylamide, N-ethyl acrylamide, N-methylol acrylamide, N-hydroxyethyl acrylamide, diacetone acrylamide, N,N-dimethyl acrylamide, N,N-diethyl acrylamide, N-ethyl-N-aminoethyl acrylamide, N-ethyl-N-hydroxyethyl acrylamide, N,N-dimethylol acrylamide, N,N-dihydroxyethyl acrylamide, t-butyl acrylamide, dimethylaminoethyl acrylamide, N-octyl acrylamide, and 1,1,3,3-tetramethylbutyl acrylamide. Other examples of monomer B include acrylic acid and methacrylic acid, itaconic acid, crotonic acid, maleic acid, fumaric acid, 2,2-(diethoxy)ethyl acrylate, hydroxyethyl acrylate or methacrylate, 2-hydroxypropyl acrylate or methacrylate, methyl methacrylate, isobutyl acrylate, n-butyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl pyrrolidone, and N-vinyl caprolactam. Combinations of various reinforcing monofunctional monomers categorized as a B monomer can be used to make the copolymer used in making the fibers of the present invention.

The acrylate copolymer is preferably formulated to have a resultant $T_g$ of less than about 25° C. and more preferably, less than about 0° C. Such acrylate copolymers preferably include about 60 parts to about 98 parts per hundred of at least one alkyl (meth)acrylate monomer and about 2 parts to about 40 parts per hundred of at least one copolymerizable reinforcing monomer. Preferably, the acrylate copolymers have about 85 parts to about 98 parts per hundred or at least one alkyl (meth)acrylate monomer and about 2 parts to about 15 parts of at least one copolymerizable reinforcing monomer.

A crosslinking agent can be used if so desired to build the molecular weight and the strength of the copolymer, and hence improve the integrity and shape of the fibers. Preferably, the crosslinking agent is one that is copolymerized with monomers A and B. The crosslinking agent may produce chemical crosslinks (e.g., covalent bonds). Alternatively, it may produce physical crosslinks that result, for example, from the formation of reinforcing domains due to phase separation or acid base interactions. Suitable crosslinking agents are disclosed in U.S. Pat. Nos. 4,379,201 (Heilman); 4,737,559 (Kellen); 5,506,279 (Babu et al.); and 4,554,324 (Husman).

This crosslinking agent is preferably not activated towards crosslinking until after the copolymer is extruded and the fibers are formed. Thus, the crosslinking agent can be a photocrosslinking agent, which, upon exposure to ultraviolet radiation (e.g., radiation having a wavelength of about 250 nanometers to about 400 nanometers), causes the copolymer to crosslink. Preferably, however, the crosslinking agent provides crosslinking, typically, physical crosslinking, without further processing. Physical crosslinking can occur through phase separation of domains which produces thermally reversible crosslinks. Thus, acrylate copolymers prepared from a crosslinker that provides reversible physical crosslinking are particularly advantageous in the preparation of fibers using a melt process.

Preferably, the crosslinking agent is (1) an acrylic crosslinking monomer, or (2) a polymeric crosslinking material having a copolymerizable vinyl group. More preferably the crosslinking agent is a polymeric material having a copolymerizable vinyl group. Preferably, each of these monomers is a free-radically polymerizable crosslinking agent capable of copolymerizing with monomers A and B. Combinations of various crosslinking agents can be used to make the copolymer used in making the fibers of the present invention. It should be understood, however, that such crosslinking agents are optional.

The acrylic crosslinking monomer is preferably one that is copolymerized with monomers A and B and generates free radicals in the polymer backbone upon irradiation of the polymer. An example of such a monomer is an acrylated benzophenone as described in U.S. Pat No. 4,737,559 (Kellen et al.).

The polymeric crosslinking materials that have a copolymerizable vinyl group are preferably represented by the general formula $X\text{-}(Y)_n\text{-}Z$ wherein: X is a copolymerizable vinyl group; Y is a divalent linking group where n can be zero or one; and Z is a monovalent polymeric moiety having a $T_g$ greater than about 20° C. and a weight average molecular weight in the range of about 2,000 to about 30,000 and being essentially unreactive under copolymerization conditions. Particularly preferred vinyl-terminated polymeric monomers useful in making the microfibers of the present invention are further defined as having: an X group which has the formula $HR^1C=CR^2$— wherein $R^1$ is a hydrogen atom or a COOH group and $R^2$ is a hydrogen atom or a methyl group; a Z group which has the formula —$\{C(R^3)(R^4)$—$CH_2\}_n$—$R^5$ wherein $R^3$ is a hydrogen atom or a lower (i.e., $C_1$–$C_4$) alkyl group, $R^5$ is a lower alkyl group, n is an integer from 20 to 500, and $R^4$ is a monovalent radical selected from the group consisting of —$C_6H_4R^6$ and —$CO_2R^7$ wherein $R^6$ is a hydrogen atom or a lower alkyl group and $R^7$ is a lower alkyl group.

Such vinyl-terminated polymeric crosslinking monomers are sometimes referred to as macromolecular monomers (i.e., "macromers"). Once polymerized with the (meth) acrylate monomer and the reinforcing monomer, a vinyl-terminated polymeric monomer of this type forms a copolymer having pendant polymeric moieties which tend to reinforce the otherwise soft acrylate backbone, providing a substantial increase in the shear strength of the resultant copolymer adhesive. Specific examples of such crosslinking polymeric materials are disclosed in U.S. Pat. No. 4,554,324 (Husman et al.).

If used, the crosslinking agent is used in an effective amount, by which is meant an amount that is sufficient to cause crosslinking of the pressure-sensitive adhesive to provide the desired final adhesion properties. Preferably, if used, the crosslinking agent is used in an amount of about 0.1 part to about 10 parts, based on the total amount of monomers.

If a photocrosslinking agent is used, the adhesive in the form of fibers can be exposed to ultraviolet radiation having a wavelength of about 250 nm to about 400 nm. The radiant energy in this preferred range of wavelength required to crosslink the adhesive is about 100 milliJoules/centimeter$^2$ (mJ/cm$^2$) to about 1,500 mJ/cm$^2$, and more preferably, about 200 mJ/cm$^2$ to about 800 mJ/cm$^2$.

The acrylate pressure-sensitive adhesives of the present invention can be synthesized by a variety of free-radical polymerization processes, including solution, radiation, bulk, dispersion, emulsion, and suspension polymerization processes. Bulk polymerization methods, such as the continuous free radical polymerization method described in U.S. Pat Nos. 4,619,979 or 4,843,134 (both to Kotnour et al.), the essentially adiabatic polymerization methods using a batch reactor described in U.S. Pat. No. 5,637,646 (Ellis), and the methods described for polymerizing packaged pre-adhesive compositions described in International Patent Application No. WO 96/07522, may also be utilized to prepare the polymer used in the preparation of the fibers of the present invention.

The acrylate pressure-sensitive adhesive compositions of the present invention can include conventional additives such as tackifiers (wood rosin, polyesters, etc.), plasticizers, flow modifiers, neutralizing agents, stabilizers, antioxidants, fillers, colorants, and the like, as long as they do not interfere in the fiber-forming melt process. Initiators that are not copolymerizable with the monomers used to prepare the acrylate copolymer can also be used to enhance the rate of polymerization and/or crosslinking. These additives are incorporated in amounts that do not materially adversely affect the desired properties of the pressure-sensitive adhesives or their fiber-forming properties. Typically, they can be mixed into these systems in amounts of about 0.05 weight percent to about 25 weight percent, based on the total weight of the composition.

Suitable polyolefin adhesives would include tackified polyolefin elastomer type adhesives, or amorphous polyalphaolefin polymers suitable for forming hot melt pressure-sensitive adhesives with or without added tackifier. Such amorphous polyalphaolefins are generally copolymers of a $C_3$ to $C_5$ linear alpha-olefin(s) and a higher alpha-olefin(s) (generally $C_6$ to $C_{10}$). Preferred are copolymers of polyolefins with polyhexene, polyheptene, polyoctene, polynonene and/or polydecene. Such amorphous polyalphaolefins are described in U.S. Pat. Nos. 4,264,576; 3,954,697; and 4,072,812 where the amorphous polyalphaolefin copolymers can be used without added tackifiers to directly form a pressure-sensitive adhesive. These amorphous copolymers generally have from 40 to 60 mole percent of the higher alphaolefin comonomer(s). However, suitable compatible tackifying resins and plasticizing oils can be used which generally correspond to those used to tackify the synthetic AB block copolymer elastomers described above. For example, suitable compatible liquid or solid tackifiers would include hydrocarbon resins, such as polyterpenes, C-5 hydrocarbon resins, or polyisoprenes. Also, resin esters of aromatic or aliphatic acids would be suitable. If these tackifiers are used in sufficient amounts, the higher alphaolefin content can be as low as 15 mole percent and still suitable pressure-sensitive adhesives can be formed.

Suitable non-adhesive materials for use in forming conjugate multicomponent fibers, for use in blends with the pressure-sensitive adhesive, or for use as separate fibers, include polyolefins, polyesters, polyalkylenes, polyamides, polystyrenes, polyarylsulfones, polydienes or polyurethanes. These materials are preferably extensible or slightly elastomeric, but could be elastomeric. Preferred are extensible or slightly elastomeric polyurethanes (e.g., "MORTHANE" PS 440-200 resin available from Morton Thiokol Corp); and polyolefins such as polyethylenes, polypropylenes, ethylene-propylene copolymers, ethylene/vinyl acetate copolymers, or metallocene-type polyethylenes having a density of greater than 0.87 grams/cm$^3$. Other suitable elastomeric materials would include metallocene-type polyethylene copolymers (apparent density less than 0.87 grams/cm$^3$); polyolefin elastomers (e.g., ethylene/propylene/diene elastomers); A–B block copolymers, as described above, having A blocks formed of poly (vinyl arenes) such as polystyrene and B blocks formed of conjugated dienes such as isoprene, butadiene, or hydrogenated versions thereof (e.g., "KRATON" elastomers available from Shell Chemical Co.); polyetheresters (such as "ARNITAL", available from Akzo Plastics Co.); or polyether block amides (such as "PEBAX", available from Atochem Co.). Blends of elastomers, blends of nonelastomers or blends of both elastomers and nonelastomers can also be used for the non-pressure-sensitive adhesive fibers, conjugate fibers or in suitable blend fibers.

Suitable polydiorganosiloxane polyurea copolymers that can be used in the preparation of fibers, preferably microfibers, according to the present invention are the reaction products of at least one polyamine, wherein the polyamine comprises at least one polydiorganosiloxane polyamine (preferably, diamine), or a mixture of at least one polydiorganosiloxane polyamine (preferably, diamine) and at least one organic amine, with at least one polyisocyanate, wherein the mole ratio of isocyanate to amine is preferably in a range of about 0.9:1 to about 1.3:1. That is, preferred polydiorganosiloxane polyurea copolymers suitable for use in the preparation of fibers according to the present invention have soft polydiorganosiloxane units, hard polyisocyanate residue units, and optionally, soft and/or hard organic polyamine residue units and terminal groups. The hard polyisocyanate residue and the hard polyamine residue comprise less than 50% by weight of the polydiorganosiloxane polyurea copolymer. The polyisocyanate residue is the polyisocyanate minus the —NCO groups and the polyamine residue is the polyamine minus the —NH$_2$ groups. The polyisocyanate residue is connected to the polyamine residue by the urea linkages. The terminal groups may be nonfunctional groups or functional groups depending on the purpose of the polydiorganosiloxane polyurea copolymers. As used herein, the term "polydiorganosiloxane polyurea" encompasses materials having the repeating unit of Formula I and low molecular weight oligomeric materials having the structure of Formula II. Such compounds are suitable for use in the present invention if they can be melt processed.

Preferred polydiorganosiloxane polyurea copolymers used in preparing the fibers of the present invention can be represented by the repeating unit:

tolylene, 4,4'-methylenediphenylene, 3,3'-dimethoxy-4,4'-biphenylene, tetramethyl-m-xylylene, 4,4'-methylenedicyclohexylene, 3,5,5-trimethyl-3-methylenecyclohexylene, 1,6-hexamethylene, 1,4cyclohexylene, 2,2,4-trimethylhexylene and mixtures thereof;

each Y is a polyvalent moiety that independently is an alkylene moiety preferably having 1 to 10 carbon atoms, an aralkylene moiety or an arylene moiety preferably having 6 to 20 carbon atoms;

each D is independently selected from the group consisting of hydrogen, an alkyl moiety of 1 to 10 carbon atoms, phenyl, and a moiety that completes a ring structure including B or Y to form a heterocycle;

B is a polyvalent moiety selected from the group consisting of alkylene, aralkylene, cycloalkylene, phenylene, polyalkylene oxide, including for example, polyethyl- (I)

where:

each R is a moiety that independently is an alkyl moiety preferably having 1 to 12 carbon atoms and may be substituted with, for example, trifluoroalkyl or vinyl groups, a vinyl moiety or higher alkenyl moiety preferably represented by the formula —R$^2$(CH$_2$)$_a$CH=CH$_2$ wherein R$^2$ is —(CH$_2$)$_b$— or —(CH$_2$)$_c$CH=CH— and a is 1, 2, or 3; b is 0, 3, or 6; and c is 3, 4, or 5, a cycloalkyl moiety having 6 to 12 carbon atoms and may be substituted with alkyl, fluoroalkyl, and vinyl groups, or an aryl moiety preferably having 6 to 20 carbon atoms and may be substituted with, for example, alkyl, cycloalkyl, fluoroalkyl and vinyl groups or R is a perfluoroalkyl group as described in U.S. Pat. No. 5,028,679 (Terae et al.), a fluorine-containing group, as described in U.S. Pat No. 5,236,997 (Fijiki), or a perfluoroether-containing group, as described in U.S. Pat. Nos. 4,900,474 (Terae et al.) and 5,118,775 (Inomata et al.); preferably at least 50% of the R moieties are methyl moieties with the balance being monovalent alkyl or substituted alkyl moieties having 1 to 12 carbon atoms, alkenylene moieties, phenyl moieties, or substituted phenyl moieties;

each Z is a polyvalent moiety that is an arylene moiety or an aralkylene moiety preferably having 6 to 20 carbon atoms, an alkylene or cycloalkylene moiety preferably having 6 to 20 carbon atoms, preferably Z is 2,6- ene oxide, polypropylene oxide, polytetramethylene oxide, and copolymers and mixtures thereof;

m is a number that is 0 to about 1000;

n is a number that is equal to or greater than 1; and p is a number that is about 5 or larger, preferably, about 15 to about 2000, more preferably, about 30 to about 1500.

In the use of polyisocyanates (Z is a moiety having a functionality greater than 2) and polyamines (B is a moiety having a functionality greater than 2), the structure of Formula I will be modified to reflect branching at the polymer backbone. In the use of endcapping agents, the structure of Formula I will be modified to reflect termination of the polydiorganosiloxane polyurea chain.

Lower molecular weight polydiorganosiloxane oligourea segmented copolymers provide a means of varying the modulus of elasticity of compositions containing this component. They can serve to either increase or decrease the modulus of the resultant composition, depending upon the particular polydiorganosiloxane mono- and di-amines employed in the preparation of the polydiorganosiloxane oligourea segmented copolymer.

The lower molecular weight polydiorganosiloxane oligourea segmented copolymers can be represented by Formula II, as follows:

(II)

-continued where:
- Z, Y, R, and D are previously described;
- each X is a monovalent moiety which is not reactive under moisture curing or free radical curing conditions and which independently is an alkyl moiety preferably having about 1 to about 12 carbon atoms and which may be substituted with, for example, trifluoroalkyl or vinyl groups or an aryl moiety preferably having about 6 to about 20 carbon atoms and which may be substituted with, for example, alkyl, cycloalkyl, fluoroalkyl and vinyl groups;
- q is a number of about 5 to about 2000 or larger,
- r is a number of about 1 to about 2000 or larger, and
- t is a number up to about 8.

These lower molecular weight polydiorganosiloxane oligourea copolymers can be used alone or in combination with the higher molecular weight polydiorganosiloxane polyurea copolymers (e.g., wherein, n in Formula I is greater than 8). For example, higher molecular weight polydiorganosiloxane polyurea copolymers can be layered with these lower molecular weight polydiorganosiloxane oligourea segmented copolymers. Alternatively, the higher molecular weight polydiorganosiloxane polyurea copolymers can optionally be blended with a lower molecular weight polydiorganosiloxane oligourea segmented copolymer which, when present, is preferably present in an amount of from about 5 parts to about 50 parts per 100 total parts of the composition. If the lower molecular weight polydiorganosiloxane oligourea copolymers are used alone, they may need to be cured (e.g., UV cured) substantially immediately upon forming the fibers (e.g., substantially immediately upon forming the web and before the web is rolled for storage) to maintain sufficient fiber integrity.

The polydiorganosiloxane polyurea copolymers can be made, stored, and then extruded into the form of fibers. If the preformed polymer does not have pressure-sensitive adhesive properties, it optionally can be coextruded with a tackifier during the fiber-forming melt process. Alternatively, the polymers can be prepared in situ (e.g., in an extruder), with or without pressure-sensitive adhesive properties, and then immediately formed into fibers.

Preferably, the polydiorganosiloxane polyurea copolymers can be made by solvent-based processes known to the art, by a solventless process or by a combination of the two. Solvent-based processes are well known in the art. Examples of solvent-based processes by which the polydiorganosiloxane polyurea copolymer useful in the present invention can be prepared include: Tyagi et al., "Segmented Organosiloxane Copolymers: 2. Thermal and Mechanical Properties of Siloxane urea Copolymers," *Polymer*, Vol. 25, December, 1984 and U.S. Pat. No. 5,214,119 (Leir et al.).

Tackifying materials for the polydiorganosiloxane polyurea copolymer, generally silicate resins, can also be added to the polymer to provide or enhance the pressure-sensitive adhesive properties of the polymer. As used herein, a pressure-sensitive adhesive possesses a four-fold balance of adhesion, cohesion, stretchiness, and elasticity, and a glass transition temperature ($T_g$) of less than about 20° C. Thus, they are tacky to the touch at room temperature (e.g., about 20° C. to about 25° C.), as can be determined by a finger tack test or by conventional measurement devices, and can easily form a useful adhesive bond with the application of light pressure.

The silicate resin can play an important role in determining the physical properties of the polydiorganosiloxane polyurea copolymer of the present invention. For example, as silicate resin content is increased from low to high concentration, the glassy to rubbery transition of the polydiorganosiloxane polyurea copolymer occurs at increasingly higher temperatures. One need not be limited to a single silicate resin as it may be beneficial to employ a combination of resins in a single composition to achieve desired performance.

The silicate resins useful in the present invention include those resins composed of the following structural units M, D, T, and Q, and combinations thereof. Typical examples include MQ silicate resins, MQD silicate resins, and MQT silicate resins which also may be referred to as copolymneric silicate resins and which preferably have a number average molecular weight of about 100 to about 50,000, more preferably about 500 to about 10,000 and generally have methyl substituents. The silicate resins also include both nonfunctional and functional resins, the functional resins having one or more functionalities including, for example, silicon-bonded hydrogen, silicon-bonded alkenyl, and silanol. MQ silicate resins are copolymeric silicate resins having $R'_3SiO_{1/2}$ units and $SiO_{4/2}$ a units. Such resins are described in, for example, *Encyclopedia of Polymer Science and Engineering*, vol. 15, John Wiley & Sons, New York, (1989), pp. 265–270, and U.S. Pat. Nos. 2,676,182 (Daudt et al.); 3,627,851 (Brady); 3,772,247 (Flannigan); and 5,248,739 (Schmidt et al.). MQ silicate resins having functional groups are described in U.S. Pat. No. 4,774,310 (Butler) that has silyl hydride groups; U.S. Pat No. 5,262,558 (Kobayashi et al.) that has vinyl and trifluoropropyl groups, and U.S. Pat. No. 4,707,531 (Shirahata) that has silyl hydride and vinyl groups. The above-described resins are generally prepared in solvent. Dried, or solventless, MQ silicate resins can be prepared, as described in U.S. Pat Nos. 5,319,040 (Wengrovius et al.); 5,302,685 (Tsumura et al.); and 4,935,484 (Wolfgruber et al.). MQD silicate resins are terpolymers having $R'_3SiO_{1/2}$ units, $SiO_{4/2}$ units, and $R'_2SiO_{2/2}$ units such as are taught in U.S. Pat No. 2,736,721 (Dexter). MQT silicate resins are terpolymers having $R'_3SiO_{1/2}$ units, $SiO_{4/2}$ units and $R'SiO_{3/2}$ units such as are taught in U.S. Pat. No. 5,110,890 (Butler) and Japanese Kokai HE 2-36234.

Commercially available silicate resins include SR-545, MQ resin in toluene, available from General Electric Co., Silicone Resins Division, Waterford, N.Y.; MQOH resins, which are MQ resins available from PCR, Inc. Gainesville, Fla.; MQR-32-1, MQR-32-2, and MQR-32-3 which are MQD resins in toluene, available from Shin-Etsu Silicones of America, Inc., Torrance, Calif., and PC403 a hydride functional MQ resin in toluene available from Rhone-Poulenc, Latex and Specialty Polymers, Rock Hill, S.C. Such resins are generally supplied in organic solvent and may be employed in compositions of the present invention as received. However, these organic solutions of silicate resin may also be dried by any number of techniques known in the art, such as spray drying, oven drying and the like, or steam separation to provide a silicate resin at substantially 100% nonvolatile content for use in compositions of the present invention. Also useful in polydiorganosiloxane polyurea copolymers of the present invention are blends of two or more silicate resins. In addition or in place of the silicate resins, organic tackifiers may be used.

When a tackifying material is included with the polydiorganosiloxane polyurea copolymer, that component preferably contains about 1 part to about 80 parts by weight tackifying material and more preferably about 15 parts to about 75 parts by weight tackifying material. The total parts by weight of the polydiorganosiloxane polyurea copolymer and the silicate resin in the combination equal 100. The optimum amount of tackifying material depends on such factors as the type and amount of reactants used, the molecular weight of the hard and soft segments of the polydiorganosiloxane polyurea segmented copolymer, and the intended use of the composition of the invention.

Fillers, plasticizers, and other property modifiers, such as flow modifiers, dyes, pigments, flame retardants, stabilizers, antioxidants, compatibilizers, antimicrobial agents, electrical conductors, and thermal conductors, may be incorporated in the pressure-sensitive adhesive composition, as long as they do not interfere in the fiber-forming melt process or do not detrimentally effect the function and functionality of the final polymer product. These additives can be blended into these systems in amounts of about 1 volume percent to about 50 volume percent of the composition of the invention.

The adhesive component region material generally comprises 1 to 60 percent of the basis weight of the nonwoven backing, preferably 15 to 40 percent.

The nonwoven backing will generally have a basis weight of from 25 to 200 g/m$^2$, preferably of the multicomponent fibers alone; however, the basis weight could be significantly higher with added particulates and/or fibers.

Commingled fibers of other types can be incorporated into the tape backing from the same die as per U.S. Pat. No. 5,601,851 above, or in a separate die which could direct the other fibers directly, or subsequently, into the fiber stream containing the adhesive multicomponent fibers prior to collection of either fiber on a collection surface. The use of multiple dies for forming commingled fibers is known in the art. Further commingled fiber webs could be formed by adding discrete staple fibers as is known in the art.

The pressure-sensitive adhesive tape layer can be continuous or intermittent and applied out of solvent or a melt phase, however it is preferrably an intermittant adhesive coating or is otherwise breathable. An intermittant coating is disclosed in U.S. Pat. Nos. 4,595,001 (Potter); U.S. Pat. No. 5,613,942; EP 353,972; and EP 91800. Preferrably the pressure-sensitive adhesive tape layer is applied from the melt phase and a particularly preferred adhesive is a fibrous nonwoven adhesive which can be formed by a melt-blown or a spun-bond process as per the preferred nonwoven tape backings where the adhesive tape layer has a basis weight of from 15 to 125 g/m$^2$. The fibrous pressure-sensitive adhesive material can be a single component fiber, or fibers, multicomponent fiber(s) or fibers formed of blend(s) or a combination thereof. With multicomponent fibers, commingled fibers, or blends, the other material components can be other pressure-sensitive adhesive materials or non-pressure sensitive adhesive materials. The other materials are generally intimately commingled with the pressure-sensitive adhesive fibers or fiber layers. The commingled pressure-sensitive adhesive fibers or microfibers and other adhesive or non-pressure-sensitive adhesive fibrous material can be present in separate individual fibers or the pressure-sensitive adhesive fibers or microfibers and the other adhesive or non-pressure-sensitive material can form distinct regions in a conjugate fiber and/or be part of a blend. For example, conjugate fibers can be in the form of two or more overlaying layered fibers, sheath-core fiber or concentric layered arrangements or in "island in the sea" type fiber structures. In this case, one component region would comprise the pressure-sensitive adhesive fiber or microfiber. Generally with any form of multicomponent conjugate fibers, the pressure-sensitive adhesive fiber component will provide at least a portion of the exposed outer surface of the multicomponent conjugate fiber. Preferably, the individual components of the multicomponent conjugate fibers will be present substantially continuously along the fiber length in discrete zones, which zones preferably extend along the entire length of the fibers. The individual fibers generally are of a fiber diameter of less than 100 microns, preferably less than 50 microns or 25 microns for microfibers.

The fibers of the fibrous pressure-sensitive adhesive tape layer can be formed by the melt blown or spun bond processes described above for forming the backing and can be formed of similar pressure-sensitive adhesive described above optionally with other adhesives and/or nonadhesives. These fibers of the pressure-sensitive adhesive tape layer can be formed in a separate step or sequentially with the formation of the backing such as disclosed in U.S. Pat. Nos. 4,655,757 or 4,778,460, the substance of which are incorporated by reference. The pressure sensitive adhesive component of a fibrous nonwoven pressure-sensitive adhesive tape layer generally comprises 100 to 50 percent of the basis weight of the fibers in the fibrous pressure-sensitive adhesive tape layer web, preferably 85 to 100 percent. Non-pressure-sensitive adhesive fibrous material, if present, and solely in the form of a blend with pressure-sensitive adhesive material, is preferably from 0 to 40 percent of the basis weight of the fibers forming the pressure-sensitive adhesive tape layer. The use of non-pressure-sensitive adhesive material with the pressure-sensitive adhesive material decreases adhesion, however, it can also increase breathability. Where the non-pressure-sensitive adhesive fibrous material is present as a discrete fiber, these fibers are generally intimately commingled with the pressure-sensitive adhesive fibers. If the non-pressure-sensitive fibrous component is present as commingled fibers, these fibers can be formed from the same die as per U.S. Pat No. 5,601,851 as described above, or in a separate die which could direct the non-pressure-sensitive adhesive fibers directly, or subsequently, into the fiber stream containing the pressure-sensitive adhesive fibers prior to collection of either fiber on a collection surface. The use of multiple dies for forming commingled fibers is known in the art. Further commingled fibers could be added as discrete staple fibers as is known in the art. The pressure-sensitive adhesive tape layer generally has a basis weight of from 5 to 200 g/m$^2$, preferably 20 to 100 g/m$^2$.

The invention nonwoven tape backing is extremely breathable generally having a moisture vapor transmission rate (MVTR) of greater than 500 gm/m$^2$/24 hrs., preferably greater than 2,000 gm./m$^2$/24 hrs. The adhesive component regions of the backing multicomponent fibers have a nominal effect on the overall tensile properties of the backing while increasing the bond of the pressure-sensitive adhesive tape layer to the backing. Generally the tape would be used with a release liner(e.g. as a tape bandage). However a release coating or treatment could be used on the surface of the backing not provided with the pressure-sensitive adhesive tape layer to permit the tape to be wound into a roll form. However this detracts from the overtaping capabilities of the tape (the ability to adhere to itself). Unexpectedly it has been found that tapes made with the invention backing can adhere to itself (overtaping) without transfer of the pressure-sensitive adhesive region from the original adhesive coated face to the opposite nonadhesive coated face, particularly if the backing is compressed (e.g. by a nip which may or may not have a gap, which gap is less than the thickness of the backing and which may be under applied pressure other than these nip rolls themselves) during or after formation of the tape.

EXAMPLES

The following examples are offered to aid in understanding of the present invention and are not to be construed as limiting the scope thereof. Unless otherwise indicated, all parts and percentages are by weight.

TEST PROTOCOLS

The following test methods were used for evaluation purposes in the examples:

Tensile Strength: ASTM Test Method No. D3759-83 using a sample width of 2.5 cm, a gauge length of 2.5 cm, and a crosshead speed of 25 cm/min. Reported is the maximum force applied to the test sample to obtain the tensile value at point of break.

Elongation at Break: ASTM Test Method No. D3759-83 using a sample width of 2.5 cm, a gauge length of 2.5 cm, and a crosshead speed of 25 cm/min. Reported is the maximum percent of stretch reached by the test sample at point of break.

Porosity: Evaluated by a procedure wherein the time (in seconds) necessary for an inner cylinder of a Gurley densometer to force 100 cc of air through a 25 mm circular sample of the fabric is determined, in a manner analogous to that described in ASTM D737-75.

MVTR: Moisture Vapor Transmission Rate evaluated in a manner analogous to that described in ASTM E 96-80 at 40° C. and expressed in grams transmitted per square meter per day.

NONWOVEN ADHESIVE WEB SAMPLES

Adhesive Sample 1

A tackified KRATON™-based nonwoven melt-blown microfiber (BMF) pressure sensitive adhesive (PSA) web was prepared using a melt blowing process similar to that described, for example, in Wente, Van A., "Superfine Thermoplastic Fibers," in *Industrial Engineering Chemistry*, Vol. 48, pages 1342 et seq (1956) or in Report No. 4364 of the Naval Research Laboratories, published May 25, 1954, entitled "Manufacture of Superfine Organic Fibers" by Wente, Van A.; Boone, C. D.; and Fluharty, E. L., except that the BMF apparatus utilized a single extruder which fed its melt stream to a gear pump that controlled the polymer melt flow. The gear pump fed a feedblock assembly that was connected to a melt-blowing die having circular smooth surface orifices (10/cm) with a 5:1 length to diameter ratio. The primary air was maintained at 220° C. and 241 KPa with a 0.076 cm gap width to produce a uniform web. The feedblock assembly was fed by a polymer melt stream (190° C.) comprised of a precompounded mixture of KRATON™ 1112 (100 parts, a styrene/isoprene/styrene block copolymer (a blend of diblock and triblock copolymer) available from Shell Chemical, Houston, Tex.), ESCOREZ™ 1310LC (80 parts, an aliphatic hydrocarbon tackifier available from Exxon Chemical Co., Houston, Tex.) and ZONAREZ™ A25 (10 parts, an alpha pinene type resin available from Arizona Chemical, Panama City, Fla.). Both the die and feedblock assembly were maintained at 180° C., and the die was operated at a rate of 178 g/hr/cm die width. The BMF-PSA web was collected on double coated silicone release paper (Daubert Coated Products, Westchester, Ill.) which passed around a rotating drum collector at a collector to die distance of 20.3 cm. The resulting BMF-PSA web had a basis weight of about 50 g/m$^2$.

Adhesive Sample 2

A tackified polyacrylate-based nonwoven BMF-PSA web was prepared using a melt blowing process similar to that described in Adhesive Sample 1, except that the feedblock assembly was fed by a polymer melt stream (190° C.) comprised of a precompounded mix of isooctyl acrylate/acrylic acid/styrene macromer (92/4/4) polymer (100 parts) and ESCOREZ™ 2393 (30 parts, a hydrocarbon tackifier available from Exxon Chemical Co.). The primary air was maintained at 223° C. and 103 KPa with a 0.076 cm gap width to produce a uniform web. Both the die and feedblock assembly were maintained at 200° C., and the die was operated at a rate of 178 g/hr/cm die width. The resulting BMF-PSA web had a basis weight of about 55 g/m$^2$.

Adhesive Sample 3

A polyacrylate-based nonwoven BMF-PSA web was prepared using a melt blowing process similar to that described in Adhesive Sample 1, except that the feedblock assembly was fed by a polymer melt stream (220° C.) comprised of an isooctyl acrylate acrylic acid styrene macromer (92/4/4). The primary air was maintained at 223° C. and 103 KPa with a 0.076 cm gap width to produce a uniform web. Both the die and the feedblock assembly were maintained at 200° C., and the die was operated at a rate of 178 g/hr/cm die width. The resulting BMF-PSA web had a basis weight of about 55 g/m$^2$.

NONWOVEN TAPE BACKING SAMPLES

Backing Sample 1

A nonwoven BMF web was prepared from polyurethane PS 440-200 resin (Morton Thiokol Corp., Seabrook, N.H.) as described in U.S. Pat. No. 5,230,701 (Meyer, et al.), which is incorporated herein by reference. The resin was melt blown at 225° C. and the die to collector distance was 15.2 cm. The resulting BMF web had a basis weight of about 100g/m$^2$.

Backing Sample 2

A nonwoven BMF web was prepared as described in Backing Sample 1, except that the PS 440-200 polyurethane resin was trickle-blended with 4% of a tan pigment (comprised of pre-blended polyurethane (80%)/pigment (20%) available as Product No. 1093538 TAN from Reed Spectrum, Minneapolis, Minn.). The resulting BMF web had a basis weight of about 104 g/m$^2$.

Backing Sample 3

A BMF-PSA web comprised of three-layer polymeric fibers was prepared using a melt blowing process similar to that described in Adhesive Sample 1, except that the BMF apparatus utilized two extruders, each of which fed its extrudate to a gear pump that controlled the polymer melt flow. The gear pumps fed a three-layer feedblock (splitter) assembly similar to that described in U.S. Pat. Nos. 3,480,502 (Chisholm, et al.) and 3,487,505 (Schrenk), which are incorporated herein by reference. The feedblock assembly was connected to a melt-blowing die having circular smooth surface orifices (10/cm) with a 5:1 length to diameter ratio. The primary air was maintained at 240° C. and 241 KPa with a 0.076 cm gap width to produce a uniform web. Both the die and feedblock assembly were maintained at 240° C., and the die was operated at a rate of 178 g/hr/cm die width.

The feedblock assembly was fed by two polymer melt streams, one being a melt stream of tackified KRATON™ 1112 (as described in Adhesive Sample 1, hereinafter designated as "KRATON" PSA) at 180° C., and the other being a melt stream of PS 440-200 polyurethane resin at 225° C. The gear pumps were adjusted to produce a 5/95 ratio of "KRATON" PSA to polyurethane resin (based on a pump ratio percent), and the BMF-PSA web was collected on a double coated silicone release paper (Daubert Coated Products, Westchester, Ill.) which passed around a rotating drum collector at a collector to die distance of 15.2 cm. The feedblock assembly split the melt streams and recombined them in an alternating manner into a three-layer melt stream exiting the feedblock assembly, the outermost layers of the exiting steam being the adhesive. The resulting BMF-PSA web had a basis weight of about 100 g/m$^2$.

Backing Sample 4

A BMF-PSA web comprised of three-layer polymeric fibers was prepared as described in Backing Sample 3, except that the "KRATON" PSA to polyurethane resin ratio was 10/90. The resulting BMF-PSA web had a basis weight of about 100 g/m$^2$.

Backing Samples 5–7

BMF-PSA webs comprised of three-layer polymeric fibers were prepared as described in Backing Sample 3, except that the PS 440-200 polyurethane resin contained 4% of the tan pigment and the "KRATON" PSA to polyurethane/pigment resin ratio was 20/80. The resulting BMF-PSA webs had basis weights of about 120 g/m$^2$ (Sample 5), 100 g/m$^2$ (Sample 6), and 75 g/m$^2$ (Sample 7).

Backing Samples 8–10

BMF-PSA webs comprised of three-layer polymeric fibers were prepared as described in Backing Samples 5–7, except that the "KRATON" PSA to polyurethane/pigment resin ratio was 30/70. The resulting BMF-PSA webs had basis weights of about 125 g/m$^2$ (Sample 8), 100g/m$^2$ (Sample 9), and 75 g/m$^2$ (Sample 10).

Backing Samples 11–13

BMF-PSA webs comprised of three-layer polymeric fibers were prepared as described in Backing Samples 5–7, except that the "KRATON" PSA to polyurethane/pigment resin ratio was 40/60. The resulting BMF-PSA webs had basis weights of about 125 g/m$^2$ (Sample 11), 100g/m$^2$ (Sample 12), and 75 g/m$^2$ (Sample 13).

Backing Sample 14

A BMF-PSA web comprised of two-layer polymeric fibers was prepared using a melt blowing process similar to that described in Backing Sample 3, except that a two-layer feedblock assembly replaced the three-layer feedblock assembly.

The feedblock assembly was fed by two polymer melt streams, one being a melt stream of "KRATON" PSA at 180° C., and the other being a melt stream of PS 440-200 polyurethane resin at 225° C. The gear pumps were adjusted to produce a 10/90 ratio of "KRATON" PSA to polyurethane and the BMF-PSA web was collected on silicone release paper as described in Backing Sample 3. The feedblock assembly split the melt streams and recombined them into a two-layer melt stream exiting the feedblock assembly. The resulting BMF-PSA web had a basis weight of about 111 g/m$^2$.

Backing Sample 15

A BMF-PSA web comprised of two-layer polymeric fibers was prepared as described in Backing Sample 14, except that the "KRATON" PSA to polyurethane/pigment resin ratio was 20/80. The resulting BMF-PSA web had a basis weight of about 122 g/m$^2$.

Backing Sample 16

A BMF-PSA web comprised of three-layer polymeric fibers was prepared as described in Backing Sample 3, except for the following. The feedblock assembly was connected to a melt-blowing die having circular smooth surface orifices (10/cm) with a 5:1 length to diameter ratio. The primary air was maintained at 238° C. and 193 KPa with a 0.076 cm gap width to produce a uniform web. Both the die and feedblock assembly were maintained at 225° C., and the die was operated at a rate of 178 g/hr/cm die width.

The feedblock assembly was fed by two polymer melt streams, one being a melt stream comprised of a 50/50 (by weight) blend of m-PE (a metallocene polyethylene available from Exxon Chemical Co.) and "KRATON" PSA at 220° C., and the other being a melt stream of PS 440-200 polyurethane resin at 220° C. The gear pumps were adjusted to produce a 20/80 ratio of "KRATON" PSA/polyethylene blend to polyurethane resin (based on a pump ratio percent), and the resulting BMF-PSA web was collected on double coated silicone release paper which passed around a rotating drum collector at a collector to die distance of 16.5 cm. The feedblock assembly split the melt streams and recombined them in an alternating manner into a three-layer melt stream exiting the feedblock assembly, the outermost layers of the exiting stream being the polyurethane. The resulting web had a basis weight of about 105 g/m$^2$.

Backing Samples Evaluations

BMF Backing Samples 2 and 5–15 were evaluated (Machine Direction) for Tensile Strength and % Elongation at Break. Results are provided in Table 1.

TABLE 1

Physical Properties of BMF Backing Samples

| Backing Sample | Fiber | PUR/ Pig. (%) | "KRATON" PSA (%) | Basis Weight (g/m$^2$) | Tensile Strength (g/2.5 cm) | % Elongation at Break |
|---|---|---|---|---|---|---|
| 2 | Single | 100 | 0 | 104 | 3242 | 437 |
| 5 | 3-Layer | 80 | 20 | 120 | 2838 | 517 |
| 6 | 3-Layer | 80 | 20 | 100 | 2411 | 500 |
| 7 | 3-Layer | 80 | 20 | 75 | 1802 | 474 |

TABLE 1-continued

Physical Properties of BMF Backing Samples

| Backing Sample | Fiber | PUR/ Pig. (%) | "KRATON" PSA (%) | Basis Weight (g/m²) | Tensile Strength (g/2.5 cm) | % Elongation at Break |
|---|---|---|---|---|---|---|
| 8 | 3-Layer | 70 | 30 | 120 | 2987 | 503 |
| 9 | 3-Layer | 70 | 30 | 100 | 2715 | 500 |
| 10 | 3-Layer | 70 | 30 | 75 | 2057 | 520 |
| 11 | 3-Layer | 60 | 40 | 120 | 2343 | 544 |
| 12 | 3-Layer | 60 | 40 | 100 | 1961 | 555 |
| 13 | 3-Layer | 60 | 40 | 75 | 1784 | 527 |
| 14 | 2-Layer | 90 | 10 | 111 | 2710 | 491 |
| 15 | 2-Layer | 80 | 20 | 122 | 2579 | 475 |

BMF Backing Samples 2, 14, and 15 were compared in evaluations for tensile-elongation properties in the machine direction, porosity using a Gurley Instrument, and Moisture Vapor Transmission Rates (MVTR). The results are provided in Table 2 and show that the adhesive-containing Backing Samples 14 and 15 are highly porous, have good "breathability" (i.e., high MVTR values), and have acceptable mechanical properties, based on tensile-elongation values, as Backing Sample 2, which contained no adhesive.

TABLE 2

Physical Properties of BMF Backing Samples

| Backing Sample | Backing Composition | Tensile Strength (g/2.5 cm) | Elongation at Break | Porosity (seconds) | MVTR (g/m²/ 24 hr) |
|---|---|---|---|---|---|
| 2 | PUR/Pigment | 3.8 | 469 | 0.2 | 8958 |
| 14 | PUR/Pig. + PSA (10%) | 2.7 | 491 | 0.2 | 8587 |
| 15 | PUR/Pig. + PSA (20%) | 2.6 | 475 | 0.2 | 8745 |

BMF Backing Samples 2, 14, and 15 were compared in peel force evaluations according to the "Peel Force" Test as described in U.S. Pat. No. 5,531,855 (Heinecke, et al.), which is incorporated herein by reference. Briefly, the Backing Samples were attached to a glass surface using double-stick tape and placed on an IMASS Peel Tester (Model No. SP-102C-3M90, manufactured by Imass Inc., Accord, Mass.). Strips (1.74-cm in width) of No. 811 SCOTCH™ Removable Magic Tape (3M Company, St. Paul, Minn.) were then adhered to the Backing Samples by passing a 2-kg roll over the tapes two times (i.e., two passes). The tape strips were peeled off the backing sample surfaces (which were firmly attached to the glass surface) at a speed of approximately 76 cm/minute. The peel force values listed below clearly show that the addition of a small amount of PSA into the polyurethane/pigment BMF nonwoven backing greatly improves adhesion strength of the backing to another adhesive surface. These results suggest that the PSA layers within the microfibers act as a "primer" within the web and can thereby enhance both 2-bond (the bond of the adhesive tape layer to the nonwoven backing) and over-taping (the bond of the adhesive layer to the nonadhesive coated face of the backing) properties.

| Backing Sample | Peel Force (g/1.74 cm) |
|---|---|
| 2 (Control) | 19 |
| 14 | 47 |
| 15 | 67 |

Example 1

The nonwoven Backing Sample 3 (BMF web comprised of 3-layer fibers containing 95% polyurethane and 5% "KRATON" PSA) was laminated to the Adhesive Sample 1 (BMF "KRATON" PSA web) by using a laboratory laminator having two rubber rollers with the bottom roller temperature set at 154° C. and the top roller temperature initially set at room temperature. The resulting adhesive tape was evaluated for adhesion to glass and stainless steel surfaces as described below.

Example 2

The nonwoven Backing Sample 4 (BMF web comprised of 3-layer fibers containing 90% polyurethane and 10% "KRATON" PSA) was laminated to the Adhesive Sample 1 (BMF "KRATON" PSA web) as described in Example 1. The resulting adhesive tape was evaluated for adhesion to glass and stainless steel surfaces as described below.

Example 3

The nonwoven Backing Sample 16 (BMF web comprised of 3-layer fibers containing 80% polyurethane and 20% "KRATON" PSA/polyethylene blend) was laminated to the Adhesive Sample 2 (BMF polyacrylate PSA web) by using a conventional calendering operation with a heated stainless steel roll (230° C.) and a rubber roll(110° C.), using a gap of 6 mils. The resulting adhesive tape had a basis weight of about 160 g/m² and was evaluated for adhesion to stainless steel, tensile strength, elongation at break, and porosity as described below.

Example 4

The nonwoven Backing Sample 16 (BMF web comprised of 3-layer fibers containing 80% polyurethane and 20% "KRATON" PSA/polyethylene blend) was laminated to the Adhesive Sample 3 (BMF tackified polyacrylate PSA web) as described in Example 3. The resulting adhesive tape had a basis weight of about 160 g/m².

Comparative Example 1

The nonwoven Backing Sample 1 (BMF polyurethane web) was laminated to the Adhesive Sample 1 (BMF "KRATON" PSA web) as described in Example 1 to afford a Comparative Example adhesive tape containing no added adhesive in the backing.

Comparative Example 2

The nonwoven Backing Sample 2 (BMF polyurethane web) was laminated to Adhesive Sample 2 as described in Example 1. The resulting adhesive tape was evaluated for adhesion to backing as described below.

Comparative Example 3

The nonwoven Backing Sample 2 (BMF polyurethane web) was laminated to Adhesive Sample 3 as described in Example 1. The resulting adhesive tape was evaluated for adhesion to backing as described below.

ADHESIVE TAPE EVALUATIONS

Adhesion to Glass

The adhesive tape samples from Example 1, Example 2, and Comparative Example 1 were cut into 2.54-cm×7.62-cm samples and then adhered to a glass surface by passing a 2-kg roll over the tapes two times (i.e., two passes). After aging for four hours, the tapes were slowly peeled off the glass by hand at speed of approximately 15 cm/minute. It was observed that the tape made from Comparative Example I (polyurethane backing containing no adhesive) left gross adhesive residue on the glass surface, whereas no residue was left by the two tapes made from Example 1 (polyurethane backing containing 5% adhesive) and from Example 2 (polyurethane backing containing 10% adhesive).

Adhesion to Stainless Steel

The procedure described above was repeated for adhesive tape samples from Example 1, Example 2, Example 3, and Comparative Example 1, except that a stainless steel surface was used in place of the glass surface. It was observed that the tape made from Comparative Example 1 left gross adhesive residue on the stainless steel surface, whereas no residue was left by the three tapes made from Example 1, Example 2, or Example 3. The adhesion strength to stainless steel was measured for the adhesive tape from Example 3 and found to be 1162 g/2.5 cm.

The results of these adhesion to glass and adhesion to stainless steel evaluations suggest that the incorporation of a small amount of adhesive into the polyurethane BMF web backing significantly improves the 2-bond strength of the resulting tape laminate, and would also be expected to enhance the over-taping performance of the tape.

Adhesion to Backing

BMF Backing Samples 2 and 16 were compared in peel force evaluations according to the "Peel Force" Test as described in U.S. Pat. No. 5,531,855 (Heinecke,et al.), which is incorporated herein by reference. Briefly, the two Backing Samples were attached to a glass surface using double-stick tape and placed on an IMASS Peel Tester (Model No. SP-102C-3M90, manufactured by Imass Inc., Accord, Mass.). Strips (1.27 cm in width) of adhesive tape samples from Comparative Example 2 and Comparative Example 3 were then adhered to the Backing Samples by passing a 2-Kg roller over the tapes two times (i.e. two passes). The tape strips were peeled off the backing sample surfaces (which were firmly attached to the glass surface) at a speed of approximately 76 cm/min. The peel values listed below show that the addition of a small amount of pressure sensitive adhesive component into the pigmented polyurethane BMF nonwoven backing greatly improves adhesion strength of the backing to another adhesive surface.

| Backing Samples | Adhesive Sample | Peel Force (g/2.54 cm) |
| --- | --- | --- |
| 2 | Comparative Example 3 | 86 |
| 16 | Comparative Example 3 | 94 |
| 2 | Comparative Example 2 | 134 |
| 16 | Comparative Example 2 | 219 |

Tensile Strength

The tensile strength (machine direction) was measured for the adhesive tape from Example 3 and found to be 3005 g/2.5 cm.

Elongation at Break

The percent elongation at break was measured for the adhesive tape from Example 3 and found to be 451%.

Porosity

The porosity was measured for the adhesive tape from Example 3 and found to be 1.3 seconds.

MVTR

The MVTR was measured for the adhesive tape from Example 3 and found to be 6166 g/m$^2$/24 hr.

We claim:

1. A pressure-sensitive adhesive coated substrate comprising a nonwoven backing substrate comprising conjugate multicomponent melt spun fibers having at least one pressure-sensitive adhesive component region forming at least a portion of the outer surface of the multicomponent fibers and at least one non-adhesive component region, the conjugate multicomponent fibers being distributed throughout the width dimension of the nonwoven backing substrate such that the adhesive component region is exposed on both outer faces of the nonwoven backing substrate, and a pressure-sensitive adhesive layer coated onto at least one face of the nonwoven backing substrate which pressure-sensitive adhesive layer has adhesive properties to the adhesive component region of the multicomponent melt spun fibers.

2. The pressure-sensitive adhesive coated substrate of claim 1 wherein the pressure-sensitive adhesive layer is breathable.

3. The pressure-sensitive adhesive coated substrate of claim 2 wherein the pressure-sensitive adhesive layer is a nonwoven web comprised of pressure-sensitive adhesive fibers.

4. The pressure-sensitive adhesive coated substrate of claim 2 wherein the nonwoven backing substrate has a basis weight of from 15 to 200 g/m$^2$.

5. The pressure-sensitive adhesive coated substrate of claim 2 wherein the nonwoven backing substrate has a basis weight of from 75 to 125 g/m$^2$.

6. The pressure-sensitive adhesive coated substrate of claim 3 wherein the nonwoven adhesive layer has a basis weight of from 15 to 125 g/m$^2$.

7. The pressure-sensitive adhesive coated substrate of claim 1 wherein the multicomponent melt spun fibers are melt blown fibers.

8. The pressure-sensitive adhesive coated substrate of claim 1 wherein the multicomponent melt spun fibers are spun bond fibers.

9. The pressure-sensitive adhesive coated substrate of claim 1 wherein the pressure-sensitive adhesive component region of the multicomponent fibers and the pressure-sensitive adhesive layer are compatible adhesives.

10. The pressure-sensitive adhesive coated substrate of claim 1 wherein the nonwoven backing substrate comprises said multicomponent fibers and commingled second fibers.

11. The pressure-sensitive adhesive coated substrate of claim 1 wherein the pressure-sensitive adhesive component region material comprises 1 to 60 percent by weight of the nonwoven backing substrate.

12. The pressure-sensitive adhesive coated substrate of claim 1 wherein the pressure-sensitive adhesive component region material comprises 15 to 40 percent by weight of the nonwoven backing substrate.

13. The pressure-sensitive adhesive coated substrate of claim 1 wherein the non-adhesive component region is selected from the group consisting of a polymer, copolymer or blend of a polystyrene, a polyolefin, a polyurethane, a polyester, a polyamide, an epoxy, a polyacrylate or a polyvinyl acrylate.

14. The pressure-sensitive adhesive coated substrate of claim 1 wherein the pressure-sensitive adhesive component region comprises a tackified polystyrene polydiene block copolymer adhesive.

15. The pressure-sensitive adhesive coated substrate of claim 1 wherein the pressure-sensitive adhesive component region comprises a polyacrylate adhesive.

16. The pressure-sensitive adhesive coated substrate of claim 1 wherein the pressure-sensitive adhesive component region comprises a tackified acrylate copolymer adhesive.

17. The pressure-sensitive adhesive coated substrate of claim 1 wherein the pressure-sensitive adhesive component region comprises a tackified polydiorganosiloxane polyurea copolymer represented by the repeating unit:

wherein:
each R is a moiety that independently is:
an alkyl moiety having 1 to 12 carbon atoms optionally substituted with trifluoroalkyl or vinyl groups;
a vinyl moiety or higher alkenyl moiety represented by the formula —$R^2(CH_2)_aCH=CH_2$ wherein $R^2$ is —$(CH_2)_b$— or —$(CH_2)_cCH=CH$— and a is 1, 2, or 3, b is 0, 3, or 6, and c is 3, 4, or 5;
a cycloalkyl moiety having 6 to 12 carbon atoms optionally substituted with alkyl, fluoroalkyl, and vinyl groups;
an aryl moiety having 6 to 20 carbon atoms optionally substituted with alkyl, cycloalkyl, fluoroalkyl and vinyl groups;
a perfluoroalkyl group;
a fluorine-containing group; or
a perfluoroether-containing group;
each Z is a polyvalent moiety that is an arylene moiety or an aralkylene moiety having 6 to 20 carbon atoms, or an alkylene or cycloalkylene moiety having 6 to 20 carbon atoms;
each Y is a polyvalent moiety that independently is an alkylene moiety having 1 to 10 carbon atoms, or an aralkylene moiety or an arylene moiety having 6 to 20 carbon atoms;
each D is independently selected from the group of hydrogen, an alkyl moiety of 1 to 10 carbon atoms, phenyl, and a moiety that completes a ring structure including Y to form a heterocycle;
B is a polyvalent moiety selected from the group consisting of alkylene, aralkylene, cycloalkylene, phenylene, polyalkylene oxide, including for example, polyethylene oxide, polypropylene oxide, polytetramethylene oxide, and copolymers and mixtures thereof;
m is a number that is 0 to 1000;
n is a number that is equal to or greater than 1: and
p is a number that is about 5 or larger 18. The pressure-sensitive adhesive coated substrate of claim 2 wherein the pressure-sensitive adhesive layer is an intermittent adhesive layer.

19. The pressure-sensitive adhesive coated substrate of claim 1 wherein the pressure-sensitive adhesive coated substrate comprises a bandage.

20. The pressure-sensitive adhesive coated substrate of claim 1 wherein the pressure-sensitive adhesive layer is a continuous adhesive layer.

21. The pressure-sensitive adhesive coated substrate of claim 1 wherein the pressure-sensitive layer is a fibrous nonwoven adhesive.

22. The pressure-sensitive adhesive coated substrate of claim 21 wherein the fibrous nonwoven adhesive comprises a tackified polystyrene polydiene block copolymer adhesive.

23. The pressure-sensitive adhesive coated substrate of claim 21 wherein the fibrous nonwoven adhesive comprises a polyacrylate adhesive.

24. The pressure-sensitive adhesive coated substrate of claim 21 wherein the fibrous nonwoven adhesive comprises a tackified polyacrylate adhesive.

25. The pressure-sensitive adhesive coated substrate of claim 21 wherein the fibrous nonwoven adhesive comprises a tackified polydiorganosiloxane polyurea copolymer represented by the repeating unit:

wherein:

each R is a moiety that independently is:
an alkyl moiety having 1 to 12 carbon atoms optionally substituted with trifluoroalkyl or vinyl groups;
a vinyl moiety or higher alkenyl moiety represented by the formula —$R^2(CH_2)_aCH=CH_2$ wherein $R^2$ is —$(CH_2)_b$— or —$(CH_2)_cCH=CH$— and a is 1, 2, or 3, b is 0, 3, or 6, and c is 3, 4, or 5;
a cycloalkyl moiety having 6 to 12 carbon atoms optionally substituted with alkyl, fluoroalkyl, and vinyl groups;
an aryl moiety having 6 to 20 carbon atoms optionally substituted with alkyl, cycloalkyl, fluoroalkyl and vinyl groups;

a perfluoroalkyl group;
a fluorine-containing group; or
a perfluoroether-containing group;

each Z is a polyvalent moiety that is an arylene moiety or an aralkylene moiety having 6 to 20 carbon atoms, or an alkylene or cycloalkylene moiety having 6 to 20 carbon atoms;

each Y is a polyvalent moiety that independently is an alkylene moiety having 1 to 10 carbon atoms, or an aralkylene moiety or an arylene moiety having 6 to 20 carbon atoms;

each D is independently selected from the group of hydrogen, an alkyl moiety of 1 to 10 carbon atoms, phenyl, and a moiety that completes a ring structure including Y to form a heterocycle;

B is a polyvalent moiety selected from the group consisting of alkylene, aralkylene, cycloalkylene, phenylene, polyalkylene oxide, including for example, polyethylene oxide, polypropylene oxide, polytetramethylene oxide, and copolymers and mixtures thereof;

m is a number that is 0 to 1000;

n is a number that is equal to or greater than 1; and p is a number that is about 5 or larger

* * * * *

UNITED STATES PATENT AND TRADEMARK OFFICE
CERTIFICATE OF CORRECTION

PATENT NO.    : 6,107,219
DATED         : August 22, 2000
INVENTOR(S)   : Eugene G. Joseph; Steven C. Stickels and Randy A. Hoff It is certified that error appears in the above-identified patent and that said Letters Patent is hereby corrected as shown below:

Title page,
Item [75] Inventors, please add -- Randy A. Hoff, Hudson, Wisconsin --

Signed and Sealed this

Twenty-seventh Day of November, 2001

Attest:

*Attesting Officer*

NICHOLAS P. GODICI
*Acting Director of the United States Patent and Trademark Office*